United States Patent [19]

Shimizu et al.

[11] Patent Number: 5,100,787

[45] Date of Patent: Mar. 31, 1992

[54] METHOD FOR PREPARING HIGHLY PURIFIED PHOSPHATIDYLINOSITOL

[75] Inventors: Shoichi Shimizu; Tsuneo Yamane; Dongxiu Li, all of Nagoya; Lekh R. Juneja, Yokkaichi, all of Japan

[73] Assignee: The Nisshin Oil Mills, Ltd., Tokyo, Japan

[21] Appl. No.: 559,047

[22] Filed: Jul. 30, 1990

[30] Foreign Application Priority Data

Aug. 30, 1989 [JP] Japan .................... 1-223886

[51] Int. Cl.$^5$ ............................ C12P 7/02; C12P 9/00
[52] U.S. Cl. ..................... 435/131; 435/155; 435/271
[58] Field of Search ............... 435/131, 155, 271

[56] References Cited

U.S. PATENT DOCUMENTS

| 4,624,919 | 11/1986 | Kokusho et al. | 435/74 |
| 4,783,402 | 11/1988 | Kokusho et al. | 435/52 |
| 4,956,286 | 9/1990 | Macrae | 435/134 |
| 4,977,091 | 12/1990 | Gilmanor et al. | 435/271 |

FOREIGN PATENT DOCUMENTS

| 62-48390 | 3/1987 | Japan. | |
| 1016595 | 1/1989 | Japan | 435/131 |

*Primary Examiner*—David M. Naff
*Assistant Examiner*—Marian C. Knode
*Attorney, Agent, or Firm*—Oblon, Spivak, McClelland, Maier & Neustadt

[57] ABSTRACT

A method for preparing highly purified phosphatidylinositol comprises the steps of treating a mixed phospholipid with a phospholipase D, then treating the product with an alkali or acidic phosphatase and separating unreated phosphatidylinositol from the reaction mixture. The method makes it possible to isolate phosphatidylinositol useful in various fields in a high purity in the order of 80 to 99%.

20 Claims, No Drawings

METHOD FOR PREPARING HIGHLY PURIFIED PHOSPHATIDYLINOSITOL

BACKGROUND OF THE INVENTION

The present invention relates to a method for preparing phosphatidylinositol in high purity and high yield starting from a mixed phospholipid. The highly pure phosphatidylinositol obtained by the present invention can widely be used as an emulsifying agent in various fields such as foods, cosmetics, agricultural chemicals and fishery and also as an emulsifying agent or a liposome-forming basic material in medicines.

Phospholipids are widely present in living things such as animals, plants, microorganisms, algae or the like principally as constituent components of cell membranes thereof and play various important roles in the living bodies. Phospholipids derived from natural sources usually comprise a mixture of phosphatidylcholine, phosphatidylethanolamine, phosphatidylinositol, phosphatidylserine, phosphatidic acid, sphingomyelin or the like. To fractionate a specific phospholipid from the mixture, there have been used various methods, for instance, solvent-fractionation techniques such as extraction fractionation with a single solvent such as methanol, ethanol, isopropyl alcohol, hexane or chloroform and recrystallization from a mixed solvent; column chromatographic fractionation techniques in which an adsorbent such as silica gel, alumina or an ion-exchange resin is employed; and fractionation techniques through formation of a composite with $CdCl_2$ or an acetylated derivative.

However, these solvent-fractionation techniques and the fractionation techniques through formation of derivatives cannot concentrate the phospholipid in a desired high purity. The combination of these methods with the column chromatographic fractionation techniques makes it possible to increase the purity of the resulting phospholipid, but the yield thereof is very low. For this reason, the thus-obtained product becomes very expensive and therefore the use thereof in an industrial scale is greatly limited. In particular, it is very difficult to isolate phosphatidylinositol from other components such as phosphatidylethanolamine and phosphatidic acid by the usual solvent-extraction method and highly purified phosphatidylinositol can be obtained only through a solvent-extraction method in which a variety of solvents are used and/or a column fractionation techniques in which a variety of solvents are used. However, in this case, the yield thereof is still very low.

On the other hand, it is also possible to chemically synthesize highly pure phospholipids and presently a variety of products chemically synthesized are industrially employed. Although chemical synthetic methods make it possible to finally prepare a single phospholipid, they suffer from various drawbacks, for instance, the deterioration and/or coloration of constitutive fatty acids or phosphoric acid esters having unsaturated bonds due to heat history during the synthesis thereof. Thus, in these methods, it is inevitable to use economically unfavorable and complicated processes for purification of the reaction products.

In addition to the foregoing methods, various attempts have been made to enzymatically convert phospholipids. For instance, Japanese Unexamined Published Patent Application (hereinafter referred to as "J. P. KOKAI") No. Sho 62-48390 discloses a method for preparing highly pure phosphatidylinositol which comprises the steps of treating a mixed phospholipid with phospholipase D derived from cabbage or rice bran to hydrolyze the phospholipid components other than phosphatidylinositol present in the mixture, extracting the reaction product with hexane and washing the extract with 5% acetic acid-containing ethanol. This method makes the best use of the characteristics of the enzyme in order to prepare phosphatidylinositol. Nevertheless, there has been a demand for the development of methods which make it possible to prepare phosphatidylinositol having a higher purity.

SUMMARY OF THE INVENTION

Accordingly a principal object of the present invention is to provide a method for easily isolating and purifying phosphatidylinositol in high purity without accompanying various drawbacks such as deterioration and degeneration of the intended product.

The foregoing and other objects of the present invention will become more apparent from the following description.

The inventors of this invention have conducted various studies to further improve the method disclosed in the above described J. P. KOKAI No. Sho 62-48390 which comprises treating a mixed phospholipid with phospholipase D to hydrolyze the phospholipid components other than phosphatidylinositol present in the mixture and isolating phosphatidylinositol from the resulting phosphatidic acid, have found out that if phosphatidic acid formed through the hydrolysis with phospholipase D is decomposed with a specific phosphatase, phosphatidylinositol can be highly purified in a very high efficiency and thus have completed the present invention based on this finding.

The present invention accordingly relates to a method for preparing highly purified phosphatidylinositol which comprises the steps of treating a mixed phospholipid with a phospholipase D, then treating the mixed phospholipid with an alkaline or acid phosphatase and isolating unreacted phosphatidylinositol from the reaction mixture.

DETAILED EXPLANATION OF THE INVENTION

The present invention will hereunder be described in more detail with reference to the preferred embodiments and Examples.

The mixed phospholipid used in the present invention is not limited to a specific one so far as it contains the intended phospholipid, i.e., phosphatidylinositol. Thus, the mixed phospholipids may be those derived from animals, plants, microorganisms, algae or the like as well as those chemically prepared. In addition, some of the mixed phospholipids sometimes include diacyl type and monoacyl type (lyso isomers) phospholipids, but they can also be used irrespective of the length of the acyl groups, presence or absence of unsaturated bonds and the number of the unsaturated bonds. In general, the mixed phospholipids derived from natural sources often contain components other than the phospholipids such as neutral fats (e. g., glycerides), sugars and glycolipids. They may be present in the starting mixed phospholipids, but it is preferable to remove them through extraction with a solvent such as a chloroform/methanol mixed solvent prior to the application of the method of this invention. The extraction with such a solvent simultaneously makes it possible to remove phosphatidylcholine.

In the method of this invention, first the foregoing mixed phospholipid as a starting material is treated with a phospholipase D. The phospholipase D does not act on phosphatidylinositol at all, in other words it does not substantially hydrolyze phosphatidylinositol and hence selectively hydrolyzes other phospholipid components such as phosphatidylcholine and phosphatidylethanolamine. More specifically, the enzyme selectively hydrolyzes phosphatidylethanolamine into phosphatidic acid.

Examples of phospholipases having such substrate-specificity include phospholipases D present in plants such as cabbage, rice bran, soybean, rapeseed, sunflower, sesame, carrot, peanut, spinach, cotton seed; phospholipases D derived from animals such as rat brain microsome and liver; phospholipases D derived from microorganisms such as microorganisms belonging to genus Streptomyces, for instance, *Streptomyces chlomofuscus*, *Streptomyces sp.* (FERM No. 6100 as disclosed in J. P. KOKAI No. Sho 58-152481), those belonging to genus Actinomadura, for instance, *Actinomadura sp.* (FERN BP-511 disclosed in J. P. KOKAI No. Sho 58-67183), those belonging to genus Nocardiopsis, for instance, *Nocardiopsis sp.* (FERM BP-512 disclosed in J. P. KOKAI No. Sho 58-63388); phospholipases D produced by microorganisms belonging to genus Micromonospora; and phospholipases D present in red algae such as *Porphyridium cruentum* and *Nemalion vermiculare*. These phospholipases can be used alone or in combination. In this respect, the phospholipases used in the present invention are not restricted to the foregoing specific examples at all.

In the method of the present invention, the foregoing hydrolyzate or the mixed phospholipid treated with the phospholipase D is then treated with an alkaline or acid phosphatase. The phosphatase selectively hydrolyzes phosphatidic acid and salts thereof, but does not act on the phospholipid components such as phosphatidylcholine, phosphatidylethanolamine and phosphatidylinositol. Examples of the alkaline phosphatases having such substrate-specificity include those derived from internal organs of animals or secretory liquids thereof such as small intestine, placenta and liver of human, small intestine, kidney and milk of cattle; kidney of pig; liver and small intestine of rat; and alkaline phosphatases derived from microorganisms such as *Escherichia coli*. On the other hand, examples of the acid phosphatases usable in the invention include those derived from prostata of human, milk of cow, bovine semen; those derived from plants such as germ of wheat, potato and sweetpotato; and those derived from microorganisms such as *Clostridium acetobutylicum* and *Schizosaccharomyces pombe*. However, the present invention is not restricted to these specific examples and these phosphatases may be used alone or in combination.

As these phospholipase D, alkaline phosphatases and acid phosphatases, those commercially available which are optionally purified or those isolated and purified from natural sources in the usual manner may be employed in the method of this invention.

The specific procedures for obtaining highly pure phospholipid from a mixed phospholipid according to the present invention will be described below in detail. The foregoing mixed phospholipid as a starting material may be used as such or it is optionally pretreated before use. The pretreatment comprises extracting a part of components present in the mixed phospholipid other than the intended component with an organic solvent such as methanol, ethanol, isopropanol, ether, chloroform, hexane or mixture thereof. The mixed phospholipid as such or thus pretreated is treated with a phospholipase D to hydrolyze the phospholipid components other than phosphatidylinositol in the presence or absence of a solvent and optionally in the presence of an additive known as an activator of the enzyme and a buffering agent with shaking or under a proper stirring condition. Examples of the solvents are dimethyl ether, diethyl ether, ethyl acetate, hexane or benzene. Examples of the optional additive known as an activator of the enzyme include sodium dodecylsulfate, cholic acid, deoxycholic acid or salts thereof, magnesium sulfate, magnesium chloride, calcium chloride or anionic surfactants. Examples of the buffering agent include acetic acid, phosphoric acid, citric acid or hydrochloric acid. The hydrolysis is performed at a pH ranging from 3 to 10, preferably 4 to 8, a temperature ranging from 10° to 70° C., preferably 20° to 40° C. for 1 to 48 hours. When a solvent is used, the reaction solution is recovered and the solvent is distilled off in the usual manner. Alternatively, when the hydrolysis is performed without using any solvent, the phospholipids are extracted with a proper solvent such as ether and the solvent is removed in the usual manner. The product hydrolyzed with the phospholipase D is then dispersed in a buffer solution to which the same additives used above are optionally added, and phosphatidic acid and salts thereof are hydrolyzed with an alkaline or acid phosphatase under the optimum conditions corresponding to each enzyme used or in the vicinity thereof. The optimum pH condition for the hydrolysis ranges from 7 to 12, preferably 7 to 10 for the alkaline phosphatase and 4 to 7, preferably 5 to 6 for the acid phosphatase. In both cases, the hydrolysis is performed at a temperature ranging from 10° to 60° C., preferably 20° to 40° C. for 1 to 48 hours. Then the product is washed, extracted and fractionated with the same organic solvent used above, or subjected to a membrane separation or a column chromatographic separation to thus give intended highly pure phosphatidylinositol. In particular, the reaction product treated with the alkaline or acid phosphatase is preferably subjected to fractionation with acetone in the usual manner. As a result, phosphatidylinositol, i.e., a phospholipid which is not hydrolyzed can be easily obtained in high purity as insolubles in acetone. The reaction processes through which the intended phosphatidylinositol can be prepared in high purity can be monitored by any means for analysis such as thin layer chromatography (TLC), high performance liquid chromatography (HPLC) and TLC/FID (Iatroscan prepared by IATRON Co., Ltd.) and whereby the reaction time can be controlled.

In the method of the present invention, the phospholipase D and alkaline or acid phosphatase are used in any amount at which the enzyme sufficiently acts on the mixed phospholipid, but the amount thereof in general ranges from 0.1 to 500 units, preferably 1 to 100 units for the phospholipase D and 1 to 1,000 units, preferably 10 to 500 units for the alkaline or acid phosphatase per g of the mixed phospholipid.

According to the method of the present invention, phosphatidylinositol can easily be isolated in a high purity (for instance, 80 to 99% purity) by hydrolyzing a variety of mixed phospholipids with a phospholipase D and an alkaline or acid phosphatase having substrate-specificity. Conventionally, phosphatidylinositol is obtained only in a low yield through fractionation using a variety of solvents, column chromatography or a complicated technique comprising a combination of these techniques. On the contrary, the present invention makes it possible to purify or isolate phosphatidylinositol, in a high purity, using widely used cheap solvents such as hexane, ethanol, acetone and chloroform.

The present invention will hereunder be described in more detail with reference to the following working non-limitative Examples. In the following Examples, phosphatidylcholine is abbreviated "PC", phosphatidylethanolamine "PE", phosphatidylinositol "PI", phosphatidylserine "PS" and phosphatidic acid "PA", respectively.

EXAMPLE 1

5 g of soybean phospholipid (PC: 32.9%; PE: 22.4%; PI: 23.6%; PA: 18.7%; and other components: 2.4%) was added to a beaker, dissolved in 50 ml of ice-cooled chloroform, 60 ml of ice-cooled methanol was added to the resulting solution with stirring to mix them and the precipitates formed were centrifuged within 10 seconds at 5000 rpm and 2° C. to collect the precipitates. To the precipitates, there were added 25 ml of ice-cooled chloroform to dissolve them and then 60 ml of ice-cooled methanol with stirring to admix these and then the mixture was centrifuged to recover precipitates. This operation was repeated two times, the solvent was distilled off under reduced pressure and the resulting precipitates were dried. The composition of the resulting extracted phospholipid was as follows: PE: 35.9%; PI: 40.5%; PA: 23.7%. Then 100 mg of the extracted phospholipid, i.e., the phospholipid free of PC was dissolved in 10 ml of diethyl ether in a reaction vessel of glass, 5 ml of 0.2M acetate buffer (pH 5.6) containing 0.06 unit/mg of the phospholipase D derived from cabbage which had been isolated and purified in the usual manner (see Lee, S. Y. et al., *J. Ferment. Technol.*, 1985, 63, p. 37) and 0.08M of calcium ions was added to the solution and the reaction was performed at 30° C. for 3 hours with stirring at 800 rpm. After the reaction, the composition of the reaction product was determined by HPLC and it was found that the product comprised PI: 56.5% and PA: 41.4%. The ether was distilled off under reduced pressure, the resulting mixture of PI and PA was dispersed in 0.06M maleate buffer (pH 6.0) while applying ultrasonic waves, 20 ml of 0.06M maleate buffer to which an acid phosphatase (derived from potato; available from Sigma Co., Ltd.) was added in an amount of 12 units per ml of the reaction solution was added to the dispersion and the reaction was carried out at 25° C. for 10 hours with stirring at 1,000 rpm, i.e., the reaction was carried out in a micellar system. The reaction solution was analyzed by TLC/FID and it was found that it comprised PI: 55.5%, PA: 1.0% and diglyceride: 41.5%. Further, the reaction solution was extracted with a Folch solution in the usual manner, the solvent was distilled off under reduced pressure, acetone was added to the resulting residue, the resulting precipitates were separated by centrifugation, washed with acetone and then dried to give 35 mg of a white solid (purified PI). The purity of PI was 98.5% and the degree of recovery of PI was high of the order of 87.5%.

EXAMPLE 2

65 mg of the phospholipid free of PC described in Example 1 was hydrolyzed with a phospholipase D in the same manner as in Example 1 except that the phospholipase D derived from *Streptomyces chromofuscus* (available from TOYO JOZO CO., LTD.) was substituted for that derived from potato used in Examples 1 and that the hydrolysis (reaction) was performed for 5 hours in 0.1M Tris-HCl buffer (pH 8.0) containing 40 mM of calcium ions. It was found that the reaction product comprised 55.0% of PI and 44.5% of PA.

The reaction product was reacted at 37° C. for 5 hours in 40 ml of Tris-HCl buffer (pH 8.8) which contained 400 mg of sodium deoxycholic acid and 40 units of the human placenta-derived alkaline phosphatase (available from Sigma Co., Ltd.), then extracted with a Folch solution and chloroform and subjected to an acetone fractionation treatment as in Example 1 to obtain 12 mg of a white solid (purified PI). The purity of PI was 98.0% and the degree of recovery of PI was 78.4%.

COMPARATIVE EXAMPLE 1

Phosphatidylinositol was prepared according to the method disclosed in J. P. KOKAI No. Sho 62-48390. More specifically, 5 g of the soybean phospholipid (PI content=23.6%) as described in Example 1 was hydrolyzed with the phospholipase D derived from cabbage (0.5 unit/mg of soybean phospholipid) for 10 hours as in Example 1. The reaction product A (4.5 g) comprised 26.0% of PI, 71.2% of PA and 2.8% of other components. 2.0 g of the reaction product A was extracted twice with 20 ml of hexane, the hexane phases were combined, concentrated, dried, then washed with 5% acetic acid-containing ethanol and dried to give 0.40 g of a white solid. The solid comprised 70.0% of PI, 29.0% of PA and 1.0% of other components and the degree of recovery of PI was 53.8%.

EXAMPLE 3

2.0 g of the reaction product A obtained in Comparative Example 1 was hydrolyzed with the foregoing potato-derived acid phosphatase under almost the same conditions used in Example 1, the resulting product was extracted twice with 20 ml of hexane, the combined hexane phase was concentrated and then washed with 5% acetic acid-containing ethanol to give 0.45 g of a white solid. The white solid comprised 97.5% of PI, 0.5% of PA and 1.0% of other components and the degree of recovery of PI was 84.4%. These results clearly indicate that the method of the present invention can provide the intended highly purified PI in a high yield in comparison with the results obtained in Comparative Example 1.

EXAMPLE 4

A mixed phospholipid was obtained from safflower in the usual manner, which comprised 15.8% of PC, 9.7% of PE, 22.7% of PI, 15.8% of PA, 3.4% of lyso-PC and 32.6% of other components. Substantially the same procedures used in Example 1 were repeated using 50 g of the mixed phospholipid originated from safflower to obtain 23 g of an extracted phospholipid substantially free of PC (PE: 25.0%; PI: 48.5%; PA: 26.1% and lyso-PC: 0.4%). Then the extracted phospholipid was treated with the phospholipase D derived from cabbage in the same manner used in Example 1, subsequently treated with the human placenta-derived alkali phosphatase used in Example 2, the reaction solution was extracted according to the precedures used in Example 1 and then the extract was subjected to acetone-fractionation to thus give 8.0 g of a white substance (PI-purity: 98.0%). The degree of recovery of PI was 70.3%.

EXAMPLE 5

To 10 g of soybean lecithin LP-20 (available from Nisshin Oil Mills, Ltd.; PC: 11.0%; PE: 23.5%; PI: 13.5%; PA: 8.5%; and other components: 43.5%), there was added the phospholipase D derived from *Streptomyces prunicolor* (available from YAKULT HONSHA CO., LTD.) in the ratio of 30 units per g of the starting substance, the reaction was performed in the two-phase system comprising 0.2M phosphate buffer (pH 7.0)-ethyl acetate (100 ml) at 30° C. for 10 hours, the solvent was distilled off, the acid phosphatase derived from bovine semen (available from Sigma Co., Ltd.) was added to the distillation residue in the ratio of 20 units per ml of the residue and the reaction was carried out at 25° C. for 24 hours in 0.2M acetate buffer (pH 5.5), i.e., in a micellar system. The reaction product was extracted three times with 300 ml of a chloroform/methanol mixture, the combined chloroform phase was concentrated, dried and acetone was added to form precipitates the precipitates were collected by centrifugation and then dried to give 1.0 g of a white solid. The solid had a PI-purity of 97.5% and the degree of recovery of PI was 72.2%.

What is claimed is:

1. A method for preparing highly purified phosphatidylinositol comprising:
   treating a mixture of phospholipids which contrain phosphatidylinositol with a phospholipase D which does not react with phosphatidylinositol for a time and under conditions effective for the hydrolysis of the phospholipids thus producing a phosphatidylinositol and phosphatidic acid mixture,
   then treating the phosphatidylinositol and phosphatidic acid mixture with an alkaline or acid phosphatase for a time and under conditions to effect the hydrolysis of phosphatidic acid, and
   isolating the phosphatidylinositol from the alkaline or acid phosphatase treated mixture.

2. The method of claim 1 wherein the treatment with the phospholipase D is performed at a pH ranging from 3 to 10 and a temperature ranging from 10° to 70° C. for 1 to 48 hours and the phospholipase D concentration in a range of 0.1 to 0.1 to 500 unit per g of the mixture of phospholipids.

3. The method of claim 2 wherein the treatment with the phospholipase D is performed at pH ranging from 4 to 8, a temperature ranging from 20° to 40° C. and a phospholipase concentration ranging from 1 to 100 units per g of the mixture of phospholipids.

4. The method of claim 1 wherein the treatment with the alkaline or acid phosphatase is performed at a temperature ranging from 10° to 60° C. for 1 to 48 hours and a phosphatase concentration ranging from 1 to 1,000 units per g of the mixture of phospholipids.

5. The method of claim 4 wherein the phosphatase is an alkaline phosphatase and the treatment with the alkaline phosphatase is performed at a pH ranging from 7 to 12 and a phosphatase concentration ranging from 10 to 500 units per g of the mixture of phospholipids 6. The method of claim 4 wherein the phosphatase is an acid phosphatase and the treatment with the acid phosphatase is performed at a pH ranging from 4 to 7, and a phosphatase concentration ranging from 10 to 500 units per g of the mixture of phospholipids.

7. The method of claim 1 wherein the phospholipase D is selected from the group consisting of those derived from cabbage, rice bran, soybean, rapesed, sunflower, sesame, carrot, peanut, spinach, cotton seed, rat brain microsome and liver; microorganisms belonging to genus Steptomyces, genus Actinomadura, genus Nocardiopsis, genus Micromonospora; and algae.

8. The method of claim 1 wherein the alkaline phosphatase is selected from the group consisting of those derived from small intestine, placenta and liver of human, small intestine, kidney and milk of cattle; kidney of pig; liver and small intestine of rat; and microorganisms and the acid phosphatase is selected from the group consisting of those derived from prostata of human, milk of cow, bovine semen; germ of wheat, potato and sweetpotato; and microorganisms.

9. A method for preparing highly purified phosphatidyl-inositol comprising:
   treating a mixture of phospholipids which contain phosphatidylinositol with a phospholipase D which does not react with phosphatidylinositol at pH of 3 to 10 at a temperture of 10° to 70° C. for 1 to 48 hours to hydrolyze the phospholipids thus producing a phosphatidylinositol and phosphatidic acid mixture, the phospholipase D being present in an amount of 0.1 to 500 units per g of the mixture of phospholipids;
   then treating the phosphatidylinositol and phosphatidic acid mixture with an alkaline or acid phosphate for a time and under conditions to effect the hydrolysis of phosphatidic acid, the phosphatase being present in an amount of 1 to 1,000 units per g of the mixture; and
   isolating the phosphatidylinositol from the alkaline or acid phosphatase treated mixture.

10. The method of claim 9 wherein mixture of phospholipids is pretreated by extracting it with an organic solvent selected from the group consisting of methanol, ethanol, isopropanol, ether, chloroform, hexane or mixture thereof.

11. The method of claim 9, wherein the treatment with the phosphatase is performed in the presence of an activator for the enzyme, a buffering agent or combination thereof.

12. The method of claim 11 wherein the activator is selected from the group consisting of sodium dodecylsulfate, cholic acid, deoxycholic acid and salts thereof, magnesium sulfate, magnesium chloride, calcium chloride and anionic surfactants and the buffering agent is selected from the group consisting of acetic acid, phosphoric acid, citric acid and hydrochloric acid.

13. The method of claim 9 wherein the product obtained after the treatment with the alkaline or acid phosphatase is treated by to acetone-fractionation.

14. The method of claim 9 wherein the treatment with the phospholipase D is performed at pH ranging from 4 to 8, a temperature ranging from 20° to 40° C. and a concentration of the phospholipase ranging from 1 to 100 units per g of the mixture of phospholipids.

15. The method of claim 9 wherein the treatment with the alkaline or acid phosphatase is performed at a temperature ranging from 10° to 60° C. for 1 to 48 hours.

16. The method of claim 15 wherein the phosphatase is an alkaline phosphatase and the treatment with the alkaline phosphatase is performed at a pH ranging from 7 to 12 and a concentration of the phosphatase ranging from 10 to 500 units per g of the mixture of phospholipids.

17. The method of claim 15 wherein the phosphatase is an acid phosphatase and the treatment with the acid phosphatase is performed at a pH ranging from 4 to 7 and a concentration of the phosphatase ranging from 10 to 500 untis per g of the mixture of phospholipids.

18. The method of claim 9 wherein the treatment with phospolipase D is performed at a pH ranging from 4 to 8 and a temperature ranging from 20° to 40° C. and the treatment with the alkaline or acid phosphatase is performed at a pH ranging from 7 to 10 or 5 to 6 and a temperture ranging from 20° to 40° C.

19. The method of claim 9 wherein the phospholipase is selected from the group consisting of those derived from cabbage, rice bran, soybean, rapeseed, sunflower, sesame, carrot, peanut, spinach, cotton seed, rat brain microsome and liver; microorganisms belonging to genus Streptomyces, genus Actinomadura, genus Nocardiopsis, genus Micromonospora; and algae.

20. The method of claim 9 wherein the alkaline phosphatase is selected from the group consisting of those derived from small intestine, placenta and liver of human, small intestine, kidney an milk of cattle; kidney of pig; liver and small intestine of rat; and microorganisms and the acid phosphatase is selected from the group consisting of those derived from prostata of human, milk of cow, bovine semen; germ of wheat, potato and sweetpotato; and microorganisms.

* * * * *